United States Patent [19]

Griffity

[11] Patent Number: 4,988,513

[45] Date of Patent: Jan. 29, 1991

[54] METHOD OF TREATING HYPOKALEMIA

[75] Inventor: Edward J. Griffity, Manchester, Mo.

[73] Assignee: Monsanto Company, St. Louis, Mo.

[21] Appl. No.: 462,195

[22] Filed: Jan. 9, 1990

[51] Int. Cl.$^5$ .................. A61K 31/66; A61K 31/80
[52] U.S. Cl. .................................. 424/439; 424/601; 424/603; 426/74
[58] Field of Search .................. 424/439, 601, 603, 74

[56] References Cited

U.S. PATENT DOCUMENTS

| 3,814,797 | 6/1974 | Kashahara et al. | 426/601 |
| 3,901,929 | 8/1975 | Nagasawa et al. | 426/613 |
| 4,115,307 | 9/1978 | McGilvery | 424/601 |
| 4,172,897 | 10/1979 | Ueno et al. | 424/601 |
| 4,216237 | 8/1980 | Smith | 426/74 |
| 4,906,482 | 3/1990 | Zemel et al. | 426/74 |

Primary Examiner—Thurman K. Page
Assistant Examiner—Amy Hulina
Attorney, Agent, or Firm—Raymond C. Loyer

[57] ABSTRACT

A method of treating hypokalemia in a human by administering Kurrol's salt in an amount effective to elevate serum potassium of the human to the range of about 3.5 mmole/l to 5.5 mmole/l.

7 Claims, No Drawings

METHOD OF TREATING HYPOKALEMIA

FIELD OF THE INVENTION

The present invention relates to a method of treating hypokalemia in a human by administering Kurrol's salt orally in an amount effective to elevate serum potassium of the human to the range of about 3.5 mmole/l to 5.5 mmole/l.

BACKGROUND OF THE INVENTION

It is well known that potassium is an essential element for the normal functioning of the human organism. When diuretics are administered, an unacceptable reduction of serum potassium, i.e., less than 3.5 mmole/l, called hypokalemia, may result. Hypokalemia is treated by supplementing dietary potassium through various means. Potassium can be supplemented intravenously. The preferred source of potassium for this treatment is potassium chloride, because of its low cost. However, when potassium chloride is taken orally, it can cause severe upper gastrointestinal symptoms. Additionally, potassium chloride has a bitter taste.

To avoid these disadvantages in oral applications, potassium chloride is used in an enteric-coated form. This approach, however, also has its disadvantages. Recent observations suggest that the dissolution of the enteric coating in the small intestine and the resulting high local concentration of potassium on the mucosa may produce ulceration, obstruction, or bleeding.

For this reason, organic potassium salts, which are more palatable and can be given without an enteric coating (and without untoward local effects on the intestine), have come into widespread use. Potassium gluconate and potassium "triplex" (citrate, acetate and bicarbonate) are the most frequently employed. The above organic potassium salts, however, have several disadvantages. Potassium gluconate delivers less than half the weight of potassium per weight of dosage than does potassium chloride, requiring larger doses of the compound. The potassium acetate used in "triplex" is a diuretic, which can exacerbate the potassium deficiency of the patient, and is also deliquesent, which makes storage and handling of the salt difficult. Additionally, the "triplex" compounds are all water soluble, which indicates that the potassium ion, which is bitter tasting, is released in the mouth.

The present invention provides a method of treating hypokalemia that overcomes the disadvantages of the above potassium sources. Kurrol's salt, also known as potassium polyphosphate or potassium metaphosphate, delivers potassium in a pleasant-tasting form that is easily handled and delivered. The salt diassociates in the stomach, not the mouth, releasing potassium ions where they can be easily assimilated. The polyphosphate is not only nonirritating, but also degrades through hydrolysis in the stomach to act as a buffer.

Phosphates as Food Ingredients, R. H. Ellinger, CRC press, 1972, discloses that calcium, iron, sodium and potassium phosphates are used to improve the nutritional properties of numerous cereal products. Kurrol's salt is presently used as a food ingredient for such uses as a meat preservative, a fungi or yeast inhibitor, or a tenderizer for the skins of fruits and vegetables. The above reference, however, fails to disclose the use of Kurrol's salt as a potassium-containing nutritional supplement to treat hypokalemia, particularly as a supplement that overcomes the disadvantages of the supplements discussed above. Additionally, the amounts of Kurrol's salt used in the above applications is typically less than 0.5 weight % of the food treated, resulting in insufficient amounts of Kurrol's salt being ingested in the normal diet to be effective to treat hypokalemia.

SUMMARY OF THE INVENTION

The present invention is a method of treating hypokalemia comprising administering Kurrol's salt in an amount effective to elevate the serum potassium level to the range of about 3.5 mmole/l to 5.5 mmole/l.

DETAILED DESCRIPTION OF THE INVENTION

The present invention is a method of treating hypokalemia by administering Kurrol's salt in an effective amount. Kurrol's salt is of the formula $(KPO_3)_n$, typically having a molecular weight of greater than 10,000. It is also known as a long-chain metaphosphate. The salt is a mixture of numerous molecules with a wide distribution of chain lengths. It is readily available from commercial sources. The pH titration curves for Kurrol's salt has two inflection points, one at pH 4.5 and a weaker one at pH 10, indicating a strong dissociation to form the potassium ion. Kurrol's salt readily dissociates in the pH range of the human stomach, i.e., from about pH 1.0 to 3.0

The amount of Kurrol's salt administered to elevate the serum potassium varies depending on the weight and sex of the individual being treated. Other factors also considered are the extent of the hypokalemic condition and whether the condition is on-going, such as induced by the daily intake of diuretics, or a one-time event, such as a catastrophic injury. It is expected that approximately 1.5 g (14 mmoles) to 4.5 g (40 mmoles) administered daily to an 150 lb (68 kg) individual will normally be an effective amount. When the hypokalemic condition is on-going, the amount may be typically administered in three doses during the day to achieve a uniformly elevated serum potassium, e.g., 0.5 g to 1.5 g administered three times a day. As long as potassium is being depleted from the body, administration of Kurrol's salt is continued.

When treating a patient suffering from a one-time event, such as a catastrophic injury, where the potassium is no longer being depleted from the body, administration of the Kurrol's salt is terminated once the serum potassium has been returned to the desired level.

The manner of delivery of the Kurrol's salt is typically oral. The natural state of the salt is a fibrous crystal. It can be administered orally as a powder, a pellet, or in a suspension, since it is not water soluble. The Kurrol's salt may be mixed with other nutrients, such as vitamins or minerals, fillers such as cellulose or calcium pyrophosphate or flavors, such as sucrose, fructose, xylitol, sorbitol, malitol, saccharine, aspartane, peppermint, spearmint or fruit. The Kurrol's salt may be suspended in water, milk or other liquids. In its unaltered natural state, the flavor of Kurrol's salt is a pleasing citrus flavor.

When used in a safe and effective amount, whether alone or in a pharmaceutically acceptable diluent, binder or liquid vehicle, hypokalemia can be successfully treated by the intake of Kurrol's salt of this invention. Because of many variables involved in human treatment, such as body weight, age, physical condition of the patient, severity of the disease or continuity of condition, a safe and effective amount must be established on an individual basis, considering the above factors as well as other health data of the person being treated. What is generally regarded as a "safe and effective amount" as used herein is meant an amount of Kurrol's salt high enough to significantly modify the condition being treated, but low enough to avoid serious side effects within the scope of sound medical judgement.

I claim:

1. A method of treating hypokalemia in a human comprising orally administering a long-chain metaphosphate of the formula $(KPO_3)_n$ having a molecular weight of about 10,000 or greater in an amount effective to elevate the serum potassium level of the human to the range of about 3.5 mmole/l to 5.5 mmole/l.

2. The method of claim 1 wherein the metaphosphate is administered in the range of about 1.5 g to about 4.5 g daily.

3. The method of claim 2 wherein the metaphosphate is administered as an undiluted solid.

4. The method of claim 3 wherein the metaphosphate is administered in three doses daily, the doses being in the range of about 0.5 g to 1.5 g each.

5. A method of treating kypokalemia in a human comprising orally administering a long-chain metaphosphate of the formula $(KPO_3)_n$ having a molecular weight of about 10,000 or greater in an amount effective to elevate the serum potassium level of the human to the range of about 3.5 mmole/l to 5.5 mmole/l wherein the metaphosphate is administered in three doses daily, the doses being in the range of about 0.5 g to about 1.5 g.

6. The method of claim 5, wherein the metaphosphate is administered as a suspension in a liquid.

7. The method of claim 5, wherein the metaphosphate is administered as a solid diluted with other nutrients, fillers or flavors.

* * * * *